US007348467B2

(12) United States Patent
De Ruiter et al.

(10) Patent No.: US 7,348,467 B2
(45) Date of Patent: Mar. 25, 2008

(54) METHOD FOR PRODUCING PLANTS WHICH ARE RESISTANT TO CLOSTEROVIRUSES

(75) Inventors: Wouter Pieter Johannes De Ruiter, Bergschenhoek (NL); Bernardus Josef Van Der Knaap, Bergschenhoek (NL); Abraham Alexander Klapwijk, Bergschenhoek (NL); René Johannes Maria Hofstede, Bergschenhoek (NL)

(73) Assignee: De Ruiter Seeds R&D B.V., Bergschenhoek (NL)

( * ) Notice: Subject to any disclaimer, the term of this patent is extended or adjusted under 35 U.S.C. 154(b) by 475 days.

(21) Appl. No.: 10/386,397

(22) Filed: Mar. 11, 2003

(65) Prior Publication Data

US 2004/0006790 A1 Jan. 8, 2004

Related U.S. Application Data

(63) Continuation of application No. PCT/NL01/00678, filed on Sep. 14, 2001.

(30) Foreign Application Priority Data

Sep. 14, 2000 (EP) .................................. 00203191

(51) Int. Cl.
*A01H 1/00* (2006.01)

(52) U.S. Cl. ....................................... 800/260; 800/265

(58) Field of Classification Search ................ 800/260, 800/265, 266, 267, 269, 307
See application file for complete search history.

(56) References Cited

FOREIGN PATENT DOCUMENTS

EP 0974672 A 1/2000
WO 0024906 5/2000

OTHER PUBLICATIONS

USDA, ARS, National Genetic Resources Program. Germplasm Resources Information Network-(GRIN). [Online Database] National Germplasm Resources Laboratory, Beltsville, Maryland. Available: http://www.ars-grin.gov2/cgi-bin/npgs/html/acchtml.pl?1193240.*

Scott et al. 1975. J. Amer. Soc. Hort. Sci. 100(5): 457-461.*

Serquen Felx et al; "Mapping and QTL . . . Markers"; Molecular Breeding, vol. 3, No. 4, 1997; pp. 257-268; XP002161522; ISSN: 1380-3743.

Livieratos I C et al; "Differentiation Between . . . Assay" Plant Pathology, GB, Oxford, vol. 47, No. 3, Jun. 1998, pp. 362-369, XP000874828.

* cited by examiner

*Primary Examiner*—David H. Kruse
*Assistant Examiner*—Keith O. Robinson
(74) *Attorney, Agent, or Firm*—Banner & Witcoff, Ltd.

(57) ABSTRACT

A method for producing cucumber plants which are resistant to cucumber closteroviruses. The method comprises the steps of providing a *Cucumis sativus* plant which contains alleles that confer resistance to the closteroviruses defined by two QTLs, crossing said *C. sativus* plant with *C. sativus* culture breeding material, collecting the seeds resulting from said cross, regenerating the seeds into plants, evaluating the plants for resistance to the closteroviruses, and identifying and selecting resistant plants. Further, a resistant cucumber plant produced by the method as well as fruit or seed produced by said plant.

6 Claims, No Drawings

METHOD FOR PRODUCING PLANTS WHICH ARE RESISTANT TO CLOSTEROVIRUSES

This application is a continuation of International Application PCT/NL01/00678 filed on 14 Sep. 2001, which designated the US, claims the benefit thereof and incorporates the same by reference.

This invention relates to a method for producing cucumber plants which are resistant to closteroviruses occurring in cucumber. Further this invention relates to cucumber plants produced by said method as well as fruit and seed produced by said plants.

BACKGROUND OF THE INVENTION

During the last fifteen years, yellowing viruses in cucumber have become a major concern of growers due to losses in production of cucumber (Hassan: A Review of a Yellowing and Stunting disorder of Cucurbits in the United Arab Emirates Emir., J. Agric. Sci (1991), 2: 1-16). The yellowing viruses are closteroviruses. In particular, two whitefly-transmitted viruses are concerned. The viruses are known as beet pseudo-yellows virus (BPYV) which is synonymous for cucumber chlorotic spot virus and which is transmitted by *Trialeurodes vaporariorum*, and cucurbit yellow stunting disorder virus (CYSDV), transmitted by *Bemisia tabaci*. The group of closteroviruses further comprises inter alia lettuce infection yellows virus (LIYV), which is a member of the Crinivirus genus of closteroviruses. The viruses are normally retained in the vectors for approx. 7 days and are transmitted by the feeding activity of the whiteflies on the plant. Common practice of disease control is by eliminating the vectors by insecticide treatment. Until now there was no known source of resistance for the pathogens and research has been done towards elimination of the vector by insecticide treatment or by breeding for resistance towards whiteflies. Until now both approaches have been unsuccessful in controlling the diseases. It is an object of the present invention to provide cucumber plants which are resistant to closteroviruses occurring in cucumber, in particular BPSV and CYSDV.

SUMMARY OF THE INVENTION

The present inventors found that the cucumber landrace Khira, PI250147, originating from Pakistan, confers resistance to BPSV and CYSDV. They crossed PI250147 with *Cucumis sativus* culture breeding material. After the cross was made, the seeds were produced on this plant and the harvested seeds were grown into plants. The plants were evaluated for resistance to BPYV and CYSDV. Plants that demonstrated resistance were backcrossed to susceptible cucumber elite lines. A Quantitative Trait Loci (QTL) analysis was performed using the AFLP fingerprinting technology, which lead to the result that the resistance is related to two QTL's.

Accordingly, the present invention provides a method for producing cucumber plants which are resistant to closteroviruses occurring in cucumber, the method comprising the steps of:

a: providing a *Cucumis sativus* plant which contains alleles that confer resistance to cucumber closteroviruses, which alleles are characterized by two Quantitative Trait Loci QTLI and QTL2 on different chromosomes, wherein QTLI is defined by the following flanking markers:

i) a marker of about 244 by consisting from 5' to 3' of an EcoRI primer having the nucleotide sequence SEQ ID NO: 1, a cucumber genomic fragment and a MseI primer having the nucleotide sequence SEQ ID NO: 2, ii) a marker of about 188 bp consisting from 5' to 3' of an EcoRI primer having the nucleotide sequence SEQ ID NO: 1, a cucumber genomic fragment and a MseI primer having the nucleotide sequence SEQ ID NO: 2, and iii) a marker of about 251 bp consisting from 5' to 3' of an EcoRI primer having the nucleotide sequence SEQ ID NO: 3, a cucumber genomic fragment and a MseI primer having the nucleotide sequence SEQ ID NO: 4, or any part of the DNA sequence as in PI250147 between the flanking markers conferring closterovirus resistance, and QTL2 is defined by the following markers:

i) a marker of about 260 bp consisting from 5' to 3' of an EcoRI primer having the nucleotide sequence SEQ ID NO: 5, a cucumber genomic fragment and a MseI primer having the nucleotide sequence ID NO: 2, and ii) a marker of about 107 bp consisting from 5' to 3' of an EcoRI primer having the nucleotide sequence SEQ ID NO: 5, a cucumber genomic fragment and a MSeI primer having the nucleotide sequence SEQ ID NO: 6, or any part of the DNA sequence as in PI250147 between the flanking markers conferring closterovirus resistance, b. crossing the *Cucumis sativus* plant provided in step a with *Cucumis sativus* culture breeding material, c. collecting the seeds resulting from the cross in step b, d. regenerating the seeds into plants, e. evaluating the plants of step d for resistance to cucumber closteroviruses; and f. identifying and selecting plants which are resistant to the cucumber closteroviruses.

The invention further provides a cucumber plant which is resistant to closteroviruses occurring in cucumber, produced by the above method, in particular a hybrid cucumber plant. Also the invention provides fruit or seed produced by said plant, and a method for producing seeds.

The term “resistance to cucumber closteroviruses” is used herein in the same meaning as it is used by a grower: a plant without visible leaf, stem or fruit symptoms caused by closteroviruses.

In cucumber the genetic variability is limited. Also, it is virtually impossible to cross *Cucumis sativus* with related species. Sources of genetic material that contain traits for (new) diseases are, therefore, difficult to obtain. However, so called landraces, which are subspecies from the commercially used long and slicer cucumbers, are maintained e.g. in East Europe: subspecies *rigidus* var ‘Europea’ and subspecies *gracilis* var. ‘Izmir and Cilicium’ (S. Neykov, Plant Genetic Resources Newsletter, 99, 1-2 (1994). In this article it was suggested that Khira PI 196289 that originates from India has potential for combinative selection especially for taste properties. Surprisingly it was found that Khira PI250147 has a novel resistance to BPYV and CYSDV between the 150 tested and known accessions. The present invention involves the successful transfer of the alleles giving resistance to BPYV and CYSDV to cucumber long and mini types commonly used in Europe and the Middle East.

In English literature the name Khira is mentioned several times (Neykov, 1994 , Dhillon, Plant Genetic Resources Newsletter, 119, 59-61, 1999) but never in relation to virus resistance. This is due to the fact that the two involved viruses are not found in Pakistan and the surrounding region.

DETAILED DESCRIPTION OF THE INVENTION

The present invention involves the creation of cucumber plants (*Cucumis sativus*) which are resistant to BPYV and CYSDV. The plants are said to be disease resistant if, when exposed to white flies containing BPYV or CYSDV, the plants fail to exhibit disease symptoms or show significantly reduced symptoms compared to susceptible plants. The plants of the present invention are novel because resistance to BPYV and CYSDV in *Cucumis sarivus* has never been shown. PI250147 contains alleles that confer resistance to BPYV and CYSDV. The alleles can be transferred successfully to elite lines by the use of a marker assisted breeding approach. Plants of the present invention can be prepared by traditional breeding techniques. For example seed from PI250147 can be used. However, due to variable disease pressure marker selection is essential for selective transfer to elite lines that can compete with known successful hybrids in the market place. The inheritance is oligogenic recessive. This means that very large populations of segregating plant generations are needed to find the less than 2 percent resistant(homozygous) plants.

EXAMPLE 1

A test was developed, using the vector whitefly (Trialeurodes and/or Bemisia). Whiteflies were allowed to feed on infected adult cucumber plants containing BPYV in a controlled greenhouse environment. Within this greenhouse 150 entries from gene banks (75 from India, 60 from China and 15 from Pakistan) were placed, with susceptible checks. Individual young plants at the 2-4 leaf stage in a tray (30 plants/$m^2$) were placed in a greenhouse surrounded by the infected plants and whiteflies. The evaluation was duplicated 2 weeks later. This trial setup lead to successful random distribution of the virus to all the young plants in the trays. After 2 weeks all the plants were planted in a vector containing greenhouse. After another 3-4 weeks the infection was scored on a scale from 1 (resistant) to 8 (susceptible). Susceptible symptoms were visible 5 -6 weeks after the start of the experiment: Surprisingly only one accession, PI250147 (Khira) proved to be resistant as visualized by the apparent absence of symptoms.

TABLE 1

| accession code | 1st experiment | 2nd experiment | average |
|---|---|---|---|
| PI 197087 | 3 | 5 | 4 |
| PI 164819 | 8 | 8 | 8 |
| PI 179676A | 7 | 8 | 7.5 |
| PI 164794 | 8 | 8 | 8 |
| PI 250147(KHIRA) | 1 | 2 | 1.5 |
| PI 211117 | 6 | 4 | 5 |
| PI 202801 | 4 | 6 | 5 |
| PI 182190 | 8 | 8 | 8 |
| PI 212599 | 8 | 5 | 6.5 |
| PI 344439 | 7 | 8 | 7.5 |
| PI 211988 | 6 | 8 | 7 |
| PI 419009 | 8 | 8 | 8 |
| PI 391573 | 7 | 8 | 7.5 |
| PI 321011 | 6 | 8 | 7 |

Table 1: Resistance towards CYSDV as scored on a scale from 1 (resistant) to 8 (susceptible) (part of the 150 accessions)

The resistant accession was crossed with elite breeding lines. The first backcross (BC1) proved to be fully susceptible to the virus illustrative of the fact that the resistance is controlled by recessive genes. Therefore, the BC1 was selfed. The selfed seed was sown in trays as described in this example and tested for resistance of the plants. The resistant plants were put in the greenhouse where visual selection was done for the phenotype equivalent to the elite line used in the initial cross. The selected individual plants were backcrossed to the original elite parent, whereafter the same breeding strategy for the transfer of recessive traits to elite lines was performed.

EXAMPLE 2

PI250147 was crossed with an elite breeding line. The F1 seeds were collected. The F1 plants were grown to maturity and the plants were selfed. The F2 seed was subsequently harvested. The F2 population was sown in the greenhouse under test conditions essentially the same as described in Example 1. From each individual plant the level of resistance was scored as well as DNA samples were obtained. On this material a Quantitative Trait Loci (QTL) analysis was performed essentially the same as described in Young, Annual Review of Phytopathology 34, 479-501 (1996). The analysis was done at Keygene, using the AFLP technology (Vos et al, Nucleic Acids Research, 1995, Vol 23, No 21, 4407-4414). The results were that the resistance is related to 3 QTL's.

One major QTL explaining 42% of the phenotypic variation (QTL1, originally in a 24 cM region containing 4 markers). A second intermediated QTL explaining 13% of the phenotype, on a different chromosome (QTL2 originally in a 24 cM region containing 7 markers) and a third QTL in a region containing 8 markers. The markers in each QTL-region were used to identify F2-individuals from the large F2, that are recombinants in one of the 3 QTL-regions. The recombinants were grouped in Near Isogenic Recombinants (NIR-)sets so that the genetic constitution of the linkage within a set only differs for the QTL that is being analyzed. By comparing the F3-phenotypes within and between sets, finemapping of QTL's was performed. The F3's from these NIR-sets were tested for resistance. We succeeded in narrowing down 2 of the 3 QTL regions: QTL 1 is still only 16 en QTL 2 only 10 cM large.

The invention claimed is:

1. A method for producing cucumber plants which are resistant to closteroviruses occurring in cucumber, the method comprising the steps of:

a. providing a plant of *Cucumis sativus* accession PI 250147, b. crossing the *Cucumis sativus* plant provided in step a with *Cucumis sativus* culture breeding material, c. collecting the seeds resulting from the cross in step b, d. regenerating the seeds into plants, e. provide one or more backcross generations by crossing the plants of step d or selfed offspring thereof with *Cucumis sativus* culture breeding material to provide backcross plants, f. selfing plants of step e and growing the selfed seed into plants, g. evaluating the plants of step f for resistance to cucumber closteroviruses, and h. identifying and selecting plants which are resistant to the cucumber closteroviruses.

2. The method of claim 1, wherein the closterovirus is Beet Pseudo-Yellows Virus (BPYV) or Cucurbit Yellow Stunting Disorder Virus (CYSDV).

3. A method for producing seeds that result in cucumber plants resistant to closteroviruses occurring in cucumber, the method comprising the steps of:

a. providing a plant of *Cucumis sativus* accession PI 250147, b. crossing the *Cucumis sativus* plant in step a with *Cucumis sativus* culture breeding material, c. collecting the seeds resulting from the cross in step b, d. regenerating the seeds into plants, e. providing one or more backcross generations by crossing the plants of step d or selfed offspring thereof with *Cucumis sativus* culture breeding material to provide backcross plants, f. selfing plants of step e to provide selfed seed, and g. selecting and identifying seeds that result in cucumber plants which are resistant to cucumber closteroviruses.

4. The method of claim 1, wherein the closterovirus is Beet Pseudo-Yellows Virus (BPYV) or Cucurbit Yellow Stunting Disorder Virus (CYSDV).

5. The method of claim 1, wherein the plants identified in step h are cucumber long or mini types.

6. The method of claim 3, wherein the seeds identified in step g result in cucumber long or mini type.

* * * * *

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
```

-continued

```
<220> FEATURE:
<223> OTHER INFORMATION: Description of Artificial Sequence: primer

<400> SEQUENCE: 1

gactgcgtac caattccc                                                18


<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 2

gatgagtcct gagtaacat                                               19


<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 3

gactgcgtac caattcaa                                                18


<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 4

gatgagtcct gagtaacac                                               19


<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 5

gactgcgtac caattcat                                                18


<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 6

gatgagtcct gagtaacgt                                               19
```